US005484911A

United States Patent [19]
Hong et al.

[11] Patent Number: 5,484,911
[45] Date of Patent: Jan. 16, 1996

[54] NUCLEOSIDE 5'-DIPHOSPHATE CONJUGATES OF ETHER LIPIDS

[75] Inventors: Chung I. Hong; Charles R. West, both of East Amherst, N.Y.; Chung K. Chu, Athens, Ga.

[73] Assignees: Health Research, Inc., Buffalo, N.Y.; University of Georgia Research Foundation, Inc., Athens, Ga.

[21] Appl. No.: 41,725

[22] Filed: Apr. 1, 1993

[51] Int. Cl.$^6$ .................................................. C07H 21/04
[52] U.S. Cl. ...................... 536/26.22; 536/27.14; 536/28.2
[58] Field of Search ............................. 536/26.2, 26.21, 536/26.22, 26.23; 514/47, 48, 51

[56] References Cited

U.S. PATENT DOCUMENTS

| | | | |
|---|---|---|---|
| 4,291,024 | 9/1981 | Turcotte | 424/180 |
| 4,471,113 | 9/1984 | MacCoss | 536/29 |
| 4,622,392 | 11/1986 | Hong et al. | 536/29 |
| 5,223,263 | 6/1993 | Hostetler et al. | 424/450 |

FOREIGN PATENT DOCUMENTS

| | | | |
|---|---|---|---|
| 0376518 | 7/1990 | European Pat. Off. | 536/26.23 |
| 0279249 | 5/1990 | German Dem. Rep. | 536/26.23 |
| 0290197 | 5/1991 | German Dem. Rep. | 536/26.23 |
| 1026594 | 7/1987 | Japan | 536/26.2 |
| 8600309 | 1/1986 | WIPO | 536/26.23 |
| 9002134 | 3/1990 | WIPO | 536/26.23 |
| 9118914 | 12/1991 | WIPO | 536/27.4 |
| 9119726 | 12/1991 | WIPO | 536/26.21 |
| 9300910 | 1/1993 | WIPO | 514/47 |

OTHER PUBLICATIONS

Kumar et al., "Equal Inhibition of HIV Replication by Stereoisomers of Phosphatidyl;–Azidothymidine," *J. Biol. Chem.*, 267(28), 20288–20292 (1992).
van Wijk et al. (II), "Spontaneous and Protein–Mediated Intermembrane Transfer of the Antiretroviral Liponucleotide 3'–Deoxythymidine Diphosphate Diglyceride," *Biochemistry*, 31, 5912–5917 (1992).
MacCoss et al., "Synthesis and Biological Activity of . . . Nucleoside–Phospholipid Prodrugs," abstract of presentation to the *4th Intl. Roundtable, Nucleoside, Nucleotides and Their Biological Applications*, Feb. 1981, Univ. of Antwerp. Belgium, p. 46.
Berdel, Wolfgang E. et al., "Cytotoxicity of Thioether–Lysophospholipids in Leukemias and Tumors of Human Origin", *Cancer Research* 43, 5538–5543 (1983).
Berdel, Wolfgang E. et al., "Therapeutic Activity of 1–B–D–Arabinofuranosylcytosine Conjugates of Lipids in WEHI–3B Leukemia in Mice", *Exp. Hematol.* 17:364–367 (1989).
Hong, Chung I. et al., "Nucleoside Conjugates. 11. Synthesis and Antitumor Activity of 1–B–D–Arabinofuranosylcytosine and Cytidine Conjugates of Thioether Lipids", *Journal of Medicinal Chemistry*, 33, pp. 1380–1386 (1990).
Snyder, Fred et al., "Requirement of Cytidine Derivatives in the Biosynthesis of O–Alkyl Phospholipids", *The Journal of Biological Chemistry*, 245, pp. 4016–41018 (1970).
Hostetler et al., "Synthesis and Antiretroviral Activity of Phospholipid Analogs of Azidothymidine and Other Antiviral Nucleosides," *The Journal of Biological Chemistry*, vol. 265, No. 11, pp. 6112–6117, 1990.
Kucera et al., "Novel Membrane–Interactive Ether Lipid Analogs That Inhibit Infectious HIV–1 Production and Induce Defective Virus Formation," *AIDS Research and Human Retroviruses*, vol. 6, No. 4, pp. 491–501, 1990.
Piantadosi et al., "Synthesis and Evaluation of Novel Ether Lipid Nucleoside Conjugates for Anti–HIV–1 Activity," *Journal of Medicinal Chemistry*, vol. 34, pp. 1408–1414, 1991.
Van Wijk et al., "Antiviral nucleoside diphosphate diglycerides: improved synthesis and facilitated purification," *Journal of Lipid Research*, vol. 33, pp. 1211–1219, 1992.
Hostetler et al., "Greatly Enhanced Inhibition of Human Immunodeficiency Virus Type 1 Replication in CEM and HT4–6C Cells by 3'–Deoxythymidine Diphosphate Dimyristoylglycerol, a Lipid Prodrug of 3'–Deoxythymidine," *Antimicrobial Agents and Chemotherapy*, vol. 36, No. 9, pp. 2025–2029, 1992.
Van Wijk et al., "Synthesis, characterization and some properties of dideoxynucleoside analogs of cytidine diphosphate diacylglycerol," *Biochimica et Biophysica Acta.*, vol. 1165, pp. 45–52, 1992.
Van Wijk et al., "Lipid conjugates of antiretroviral agents: release of anti–retroviral nucleoside monophosphates by a nucleoside diphosphate diglyceride hydrolase activity from rat liver mitochondria," *Biochimica et Biophysica Acta.*, vol. 1084, pp. 307–310, 1991.
Van Wijk et al., "Cytidine diphosphate diglyceride analogs of antiretroviral dideoxynucleosides: evidence for release of dideoxynucleoside–monophosphates phospholipid biosynthetic enzymes in rat liver subcellular fractions," *Biochimica et Biophysica Acta.*, vol. 1086, pp. 99–105, 1991.

*Primary Examiner*—Douglas W. Robinson
*Assistant Examiner*—L. Eric Crane
*Attorney, Agent, or Firm*—Michael L. Dunn

[57] ABSTRACT

A compound which exhibits antiviral activity having the formula:

$$\begin{array}{c} \quad\quad\quad\ \ O\quad\quad CH_2-A-R_1 \\ \quad\quad\quad\ \ \| \quad\quad\ \ | \\ R_2-C-O-C-H \quad\ \ O \quad\ \ O \\ \quad\quad\quad\quad\quad | \quad\quad\ \ \| \quad\ \ \| \\ \quad\quad\quad\quad CH_2-O-P-O-P-O-\text{Nucleoside} \\ \quad\quad\quad\quad\quad\quad\quad\ \ | \quad\quad\ | \\ \quad\quad\quad\quad\quad\quad\quad\ \ O^- \quad\ \ O^- \end{array}$$

wherein;

$R_1$ is selected from the group consisting of alkyls and alkenyls containing from 8 to 22 carbon atoms;

A is selected from the group consisting of O and S atoms;

$R_2$ is selected from the group consisting of alkyls and alkenyls containing from 8 to 22 carbon atoms; and the Nucleoside is selected from the group consisting of 2',3'-dideoxynucleosides, 3'-azido-2',3'-dideoxynucleosides, and 2',3'-didehydro-2',3'-dideoxynucleosides.

13 Claims, 7 Drawing Sheets

NUCLEOSIDE 5'-DIPHOSPHATE CONJUGATES OF ETHER LIPIDS

The invention described herein was made in the course of work partially supported by a grant from the National Institute of Allergy and Infectious Diseases, National Institutes of Health (Grant Nos. AI CA 25538-01, AI 27697-01 and AI 27697-01 AI) Grant Number 5 ROI AI27697.

BACKGROUND OF THE INVENTION

1. Field of the Invention

This invention relates to conjugates of anti-HIV nucleosides and antiviral ether and thioether lipids working as both prodrug and combination chemotherapy with two or more antiviral moieties with different target sites, exhibiting enhanced antiviral activity.

This invention also relates combination chemotherapy of micellar formulation of the conjugate and other antiviral drugs.

2. Brief Description of the Background

The human immunodeficiency virus (HIV), an enveloped single-stranded RNA virus, is the severe causative agent of acquired immune deficiency syndrome (AIDS). Efforts to develop drugs and vaccines that combat AIDS have resulted in dozens of potential treatments, which are in clinical and preclinical study. An unprecedented triple challenge is 1) stop the HIV, 2) restore the damaged immune system, and 3) treat any opportunistic infections. In view of the etiologic role of HIV, antiviral agents which inhibit HIV replication can be considered as a viable approach towards an effective chemotherapy of AIDS. Major steps in the replicative cycle of HIV are absorption, penetration, uncoating, reverse transcription, circulation, integration, translation, assembly and budding. For inhibitors of HIV replication, absorption, reverse transcription, transactivation, and budding have been identified or postulated as target. The majority of the anti-HIV agents appears to act at the reverse transcriptase level, and most of them belong to the class of 2',3'-dideoxynucleosides. To date, 3'-azido-3'-deoxythymidine (AZT), 2',3'-dideoxyinosine (ddI), and 2',3'-dideoxycytidine (ddC) are the only compounds licensed for clinical use in the treatment of AIDS In addition to these compounds, various other 2',3'-dideoxynucleoside analogs, 3'-substituted 2',3'-dideoxynucleoside, and 2',3'-didehydro-2',3'-dideoxynucleoside have proven to be potent and selective inhibitors of HIV replication with selectivity All 2',3'-dideoxynucleoside analogs are assumed to act in a similar fashion as AZT, which implies that they need first to be converted intracellularly to their 5'-triphosphates. These dideoxynucleoside 5'-triphosphates can compete with normal 2'-deoxynucleotides for binding to reverse transcriptase or they can be incorporated into the growing DNA chain to bring about termination of viral DNA synthesis. And 2',3'-dideoxynucleoside 5'-triphosphates have higher affinities for HIV reverse transcriptase than for cellular DNA polymerase $\alpha$. If, in fact, the 2',3'-dideoxynucleosides are degraded by catabolic enzymes, i.e. deaminases or phosphorylases, before being anabolized by the kinases, they may never reach the 5'-triphosphate stage.

Membrane-active ether lipid analogs of platelet-activating factor selectively inhibit HIV-1 plaque formation ($IC_{50}$ 0.2–1.4 µM) and the inhibition correlates with inhibition of infectious HIV-1 production, which indicate that the ether lipid analogs inhibit both HIV-induced cytopathology and infectious virus multiplication by inducing defective intracytoplasmic vacuolar HIV-1 formation in T-cells. Being membrane interactive, the ether lipid analogs are ideally suited for combination chemotherapy with DNA-interactive anti-HIV nucleoside analogs. The combination of ether lipid analog and AZT produced an apparent synergistic action in suppressing infectious HIV-1 replication (Kucera, et al., *AIDS Research and Human Retroviruses* 6, 491, 1990).

In order to facilitate the mechanism of action of antitumor nucleoside, 1-β-D-arabinofuranosylcytosine (ara-C), and to overcome its degradation by catabolic enzymes, a series of new lipophilic biotransformed prodrugs of ara-C were synthesized by covalently conjugating ara-C with phosphatidic acids via a naturally occurring phosphate linkage. These liponucleotides include the ara-C conjugates of 1,2-diacyl (Hong, C. I. et al., *Cancer Drug Delivery* 1, 181, 1984), 1-O-alkyl (ether) (Hong, C. I. et al., *J. Med. Chem.* 29, 2038, 1986), and 1-S-alkyl (thioether) (Hong, C. I. and West, C. R., U.S. Pat. No. 4,622,392, Issued Nov. 11, 1986) phospholipids. These conjugates have ara-C substituted for cytidine or both ara-C and ether (or thioether) lipid substituted for cytidine and diacylglyceride in cytidine diphosphate diacylglyceride, a precursor for membrane phosphatidylinositol and cardiolipin. The rationale is that the conjugates are not only prodrugs of ara-C but also may generate two cytotoxic principles (ara-CTP and ether or thioether lipid) with different target sites, nucleic acid synthesis and membrane, inside a neoplastic cell. Most of the ara-C conjugates produce significant increases in the life span and long-term survival of mice with L1210 and P388 leukemia, independent of treatment schedule. Among them, ara-CDP-DL-PTBA (hereinafter referred to as Cytoros), a conjugate of thioether phospholipid, is the most effective of those tested (Hong, C. I. *Drugs of the Future* 15, 245, 1990). Cytoros showed considerably higher efficacy than ara-CDP-L-dipalmitin, conjugate with 1-O-acyl phospholipid, against myelomonocytic WEHI-3B leukemia in mice. Cytoros has a rather broad spectrum of therapeutic activity in mice with various solid tumors such as colon 26 carcinoma, M5076 sarcoma, Lewis lung carcinoma, and C-1300 neuroblastoma. Furthermore, this drug displayed antimetastic activity in mice with M5076 sarcoma and Lewis lung carcinoma. Cytoros showed a strong antitumor activity against human colorectal cancer xenografts and PSN-1 human pancreatic tumor in nude mice. Cytoros alone and in combination with VP-16 markedly retarded both primary and lymph node metastasis of rat mammary carcinoma SMT-2A. Thus, Cytoros seems to be not only highly active by itself, but also serves as a powerful and selective drug delivery system for the eradication of metastatic cancer. The mode of action of Cytoros and other ara-C conjugates of phospholipids remains largely unknown. They may act as lipophilic prodrugs with sustained release of ara-C or facilitate transfer of the active moiety across tumor cell membranes because of their lipophilic nature. Evidence from the studies with L1210 leukemia in mice demonstrated that the administration of Cytoros led to more prolonged plasma ara-C concentration and intracellular retention of ara-CTP than those resulting from ara-C. This may account for its increased therapeutic effectiveness, since it has been shown that increased leukemic cell retention of ara-CTP correlates with therapeutic response. Further, other possible pharmacologically favorable properties of the conjugates as compared to the parent drug include resistance to hydrolysis by cytidine deaminase, rapid interaction with serum lipoproteins, rapid uptake by cells, and effects on lipid biosynthesis. Cytoros showed a selective cytotoxicity to L1210 leukemic cells compared to normal mouse bone marrow cells.

Previously, anti-HIV nucleoside conjugates of phospholipids (diacyl, ether thioether, and amido) have been reported. Dimyristoyl-phosphatidylAZT, dimyristoylphosphatidylddT, dimyristoylphosphatidylddC, and AZT dipalmitoylglycerol were encapsulated in liposomes and these liposomal liponucleotides were shown to have antiretroviral activity in HIV-infected U937 ($IC_{50}$ 0.2–12 μM) and CEM cells ($IC_{50}$ 1.7–22 μM) (Hostettler, K. Y. et al., *J. Biol. Chem.* 265, 6112, 1990). AZT and ddI conjugates of amidoalkyl, oxyalkyl, and thioalkyl ether lipids through phosphate and phosphonate linkages showed promising in vitro activity ($IC_{50}$ 0.02–1.56 μM) with 5–10 fold reduction in cell cytotoxicity compared to AZT alone (Piantadosi, C. et al., *J. Med. Chem.* 34, 1408, 1991). Hostettler's conjugates are those with non-antiretroviral diacylglycerides with phosphodiester or pyrophosphate diester bond. Thus, these conjugates are considered to be simple prodrugs of anti-HIV nucleosides. Since the majority are conjugates with a phosphodiester (monophosphate) bond, they cannot form micelles by sonication; therefore, they must be encapsulated in liposomes for testing. Also, Piantadosi's conjugates contain monophosphate or phosphonate bonds which cannot be formulated in micellar solution by sonication.

BRIEF DESCRIPTION AND OBJECTS OF THE INVENTION

The present invention describes anti-HIV conjugates coupled with another antiviral ether and thioether lipids with a pyrophosphate diester (diphosphate) bond, which are analogs of naturally occurring cytidine 5'-diphosphate dicylglycerol (CDP-DG), an intermediate in the biosynthesis of acidic phospholipids such as phosphatidylinositol, phosphatidylglycerol, and diphosphatidylglycerol (cardiolipin). Thus, these conjugates form micelles by sonication and carry both an anti-HIV nucleoside and a membrane-active antiviral ether lipid analog. The inventive rationale behind these conjugates is 1) ether lipid-nucleoside conjugates might allow a larger concentration of drug to enter the cell due to the lipophilic nature of the ether lipid, 2) hydrolysis of the conjugate by cellular enzymes (e.g. phosphatases) might result in the slow release of nucleoside 5'-monophosphate into treated cells, possibly reducing resistance development to the nucleoside, 3) the degradative metabolism of the conjugate might release two active species (nucleoside 5'-monophosphate and ether lipid analogs), and 4) the potential benefits of combination chemotherapy of other lipophilic anti-HIV drugs solubilized into micelles of the conjugates.

It has been shown that anti-HIV nucleosides conjugates of diacylglycerides with diphosphate bond, e.g., AZT diphosphate diglyceride (AZTDP-DG), ddCDP-DG, and ddTDP-DG, can substitute to varying extents for CDP-DG in the biosynthesis of phosphatidylinositol, phosphatidylglycerol or diphosphatidylglycerol, thereby causing the release of nucleoside 5'-monophosphates which were detected in rat liver subcellular fractions. The release of the 5'-monophosphates from the conjugates by rat liver mitochondrial enzymes was also demonstrated. These results support the rationale that the conjugates may provide cells with a depot form from which the antiviral drug can be released in 5'-monophosphate forms, thus bypassing the initial phosphorylation of free anti-HIV nucleosides. Thus, the present conjugates may also release the nucleoside 5'-monophosphates and the ether lipid moieties intracellularly by metabolic degradation. Therefore, the present conjugates should not be considered as simple prodrugs of the anti-HIV nucleoside; rather, they should be referred to as biotransformed prodrugs.

The conjugates can be further modified by introducing more antiviral principles in the molecules. Myristic acid, a 14-carbon saturated fatty acid, is covalently linked by an amide bond to the N-terminal glycine residue of a number of eukaryotic cellular and viral proteins. Myristic acid appears to be critical for the assembly of certain retroviruses and for targeting certain oncoproteins and myristoylation is required to target newly formed virus capsids to plasma membrane where maturation and budding occur. Heteroatom-substituted analogs of myristate inhibit replication of HIV-1 and Moloney murine leukemia virus that depend on N-myrisoylation of their gag polyprotein precursors for assembly. The selective nature of their effects together with their apparent lack of cellular toxicity suggest that these compounds may represent an additional and useful class of antiviral agents. 13-Oxamyristic acid (12-methoxydodecanoic acid) appears to be the most effective, producing a concentration-dependent decrease in reverse transcriptase activity, p24 levels, and syncytia formation (Bryant, M. L. et al., *Proc. Natl. Acad. Sci. USA* 86, 8655, 1989). The antiviral activity of mono and polyunsaturated fatty acids has been known for over a decase. They are active against a number of enveloped viruses and thought to work in part by physical disruption of the virus particle. It has also been demonstrated that unsaturated and saturated alcohols of moderate lengths exert a substantial inhibitory effect on replication of lipid-enveloped viruses. 1-Docosanol, 22-carbon-long saturated alcohol, inhibits herpes simplex and respiratory syncytial viral replication by interfering with the early intracellular events surrounding viral entry into target cells. 1-Docosanol may provide a broad spectrum activity against many different viruses, especially those with lipid-containing envelopes (Katz, et al., *Proc. Natl. Acad. Sci. USA* 88, 10825, 1991).

Therefore, the anti-HIV nucleoside conjugates of ether lipids can be modified by substituting 1-docosanol at sn-1 of the glycerol moiety and polyunsaturated fatty acid or 13-oxamyristic acid at the sn-2. These conjugates carry 1) anti-HIV nucleoside, 2) membrane-active anti-HIV ether lipid analog, 3) anti-HIV 13-oxamyristic acid, and likewise 4) antiviral polyunsaturated fatty acid and 1-docosanol.

As illustrated in FIG. 1, the intact conjugate may work as a biotransformed prodrug with favorable properties such as sustained release of the nucleoside, resistance to hydrolysis by catabolic enzymes, and target specific delivery—selectivity. The conjugate may be metabolized in the cells to the nucleoside 5'-monophosphate and the glycerol or its 3'-phosphate. The 5'-nucleotide may be further phosphorylated to the nucleoside 5'-triphosphate, which inhibits the viral reverse transcriptase. The phosphatidic acid may be matabolized to 1-O-(or S)-alkyl-2-O-acylglycerol (or-1-thioglycerol) by phosphohydrolase and the latter may serve as a substrate for cholinephosphotransferase (EC 2.7.8.2) to produce 1-O-(or S)-alkyl-2-acylphosphatidylcholine. This might be then deacylated to the corresponding lysophosphadityl-choline via a phospholipase $A_2$ reaction and release the fatty acid such as 13-oxamyristic acid or polyunsaturated fatty acid. The lysophosphocholine analog works both as an anti-HIV agent and a substrate of alkyl cleavage enzyme (tetrahydropteridine-dependent alkyl monooxygenase) releasing antiviral 1-docosanol or other long-chain alcohol.

It is well documented that HIV binds to the molecule known as $CD_4$ antigen which is found primarily on the cells of the immune system. Thus, the loss of these $T_4$ bearing helper lymphocytes causes deterioration of the immune system. It has been suggested that the first contact of HIV with its cellular receptor is mediated by proteins encoded by viral envelope (env) gene and primarily env gene product is a 160 kDa glycoprotein which is proteolytically cleaved producing a major exterior glycoprotein gp 120 and a small fragment of glycosylated gp41. It has been further documented that gp120 is essential for the interaction of the virus with $CD_4$ receptor. It has been reported that phosphatidic acids inhibit the activity of galactosyltransferase and other phospholipids also influence the activities of various glycosyltransferases. Thus, one of the hydrolysis products of the conjugate, the phosphatidic acid, might interfere with biosynthesis of the glycoprotein and prevent the interaction of the virus with $CD_4$ receptor. Furthermore, since AL721 (lipid mixture of neutral glycerides, phosphatidylcholine, and phosphatidyl-ethanolamine in 7:2:1 ratio) interferes with HIV infectivity, the proposed conjugates of phospholipids are particularly of interest. The neutral glycerides and various phospholipids could be obtained intracellularly from the conjugates.

In addition to the proposed biochemical pharmacologic aspect of the conjugates, their pharmaceutical advantages also support this program. Monocytes and macrophages represent a significant reservoir of HIV infection in the human host, while macrophages take up the bulk of parenterally administered liposomes. The aggregation of single molecules of a certain type, when dissolved in water to form a particle of colloidal dimension, is called a micelle. Since the conjugates with a pyrophosphate diester bond (diphosphate) form micelles by sonication of their aqueous suspension (size 0.01–0.04 µM), it is anticipated that the conjugates in micelles like those in liposomes will be taken up in large proportion by the macrophages infected by HIV. This property would appear to make the conjugates promising candidate agents with a special potential to target drug directly to the macrophage reservoir of HIV infection, which reduces the toxicity of the antiviral nucleosides to other cells.

The increased solubility in a micellar solution of an organic substance, insoluble or sparingly soluble in water, is a property which has been applied to drug formulations. Micellar solution of the antitumor nucleoside conjugates solubilizes nitrosoureas (BCNU and MeCCNU) and other water insoluble antitumor drugs and these micelle-solubilized lipophilic drugs have exhibited an exceptional antitumor activity exceeding those of the conjugate and the lipophilic drug (Hong, C. I. *Drugs of the Future* 15, 245, 1990). Some of the advantages of the micelle-solubilized drug are the release of more drug, the release of the same amount of drug over a longer interval, and the release of drug at more nearly constant rate than if micelles are absent. Thus, water insoluble or sparingly soluble anti-HIV drug could be mixed with the micellar formulation of the conjugate and the micelle-solubilized anti-HIV agents would have all the advantages mentioned above, as well as better therapeutic indices as compared to previous micelle-solubilized anticancer drugs.

In view of the state of the art, it is clear that there remains a strong need for new antiviral agents, especially those with low toxicity to normal cells. More particularly, because of the high mortality of AIDS and the lack of an effective treatment for this disease, there remains a great need for development of new low toxicity agents for such treatment because AIDS patients require a long term therapy, possibly an entire life span. It was in this context that the present invention was achieved.

It is therefore an object of the present invention to provide new antiviral compounds having low toxicity towards normal cells.

It is a further object of this invention to provide compounds for inhibiting the growth of human immunodeficiency virus (HIV).

It is yet another object of the present invention to provide compositions for the treatment of individuals afflicted with AIDS.

Another object of this invention is to provide a method for the prevention and treatment of infection by HIV.

SUMMARY OF THE INVENTION

The above features and advantages of the present invention are realized by providing compounds of the general formula:

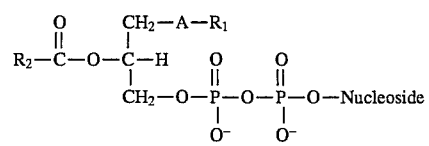

wherein:

$R_1$ is selected from the group consisting of alkyls and alkenyls containing from about 8 to about 22 carbon atoms;

A is selected from the group consisting of O and S atoms;

$R_2$ is selected from the group consisting of alkyls and alkenyls containing from about 8 to about 22 carbon atoms; and the Nucleoside is selected from the group consisting of 2',3'-dideoxynucleosides, 2',3'-azido-2',3'-dideoxynucleosides, 2',3'-didehydro- 2',3'-dideoxynucleosides Furthermore, the $R_2$ alkyls are preferably heteroatom-containing alkyls such as $CH_3$—O—$(CH_2)_{10}CH_2$ and $CH_3CH_2$—S—$(CH_2)_{10}$; the $R_2$ alkenyls are preferably polyunsaturated alkenyls such as $CH_3(CH_2)_2(CH_2CH=CH)_2(CH_2)_7$, $CH_3(CH_2CH=CH)_3(CH_2)_7$ and $CH_3(CH_2)_4(CH=CHCH_2)_4CH_2CH_2$; the 2',3'-dideoxynucleosides are preferably 2',3'-dideoxycytidine (ddC), 2',3'-dideoxyinosine (ddI), 2',3'-dideoxyadenosine (ddA), and 3'-deoxythymidine (ddT); the 3'-azido- 2',3'-dideoxynucleosides are preferably 3'-azido-3'-deoxythymidine (AZT) and 3'-azido-2',3'-dideoxyuridine (AZddU); and the 2',3'-didehydro-2',3'-dideoxynucleosides are preferably 2',3'-didehydro-3'-deoxythymidine (D4T) and 2',3'-didehydro- 2',3'-dideoxycytidine (D4C).

Additionally, a compound of the present invention can be converted into the base addition salt via reaction with base, both inorganic and organic.

Due to their antiviral activity, the compounds of this invention are useful as anti-HIV, antiretroviral, and antiviral agents, particularly anti-AIDS agents (see Biological Data), and can be administered via a pharmaceutically-acceptable carrier or in micellar solution, either alone or in combination with other antiviral agents.

The compounds of this invention are effective against the same kinds of virus growth as their corresponding nucleoside and exhibit a significant improvement on the therapeutic indices of the parent compounds by acting as biotransformed prodrugs with additive or even synergistic effects from the parent nucleoside and ether or thioether lipid moiety.

It can be seen from the general formula that a number of innovations may be tailored into the parent molecular structure, including:

(a) utilization of any combination of single or multi-species fatty chains varying in length and degree of unsaturation;

(b) inclusion of ether at the glycerol-2 position;

(c) variations in the nucleoside moiety.

The physicochemical and metabolic properties of the compounds can be markedly altered by structural modifications in the nature of the nucleoside stereochemistry. As can be appreciated, antiviral nucleotide ether or thioether lipid analogues, as intact molecules, cannot be properly considered as merely derivatives or forms of existing antiviral nucleotides or ether or thioether lipids, but rather are a distinct class of compounds.

The synthesis of the present compounds involve adaptations of reactions of multi-species ether or thioether phosphatidic acid with nucleotide morpholidates as described in Example 1.

Nucleotides in general are prepared from corresponding nucleosides by direct phosphorylation using $POCl_3$ and trialkyl phosphate or 2-cyanoethyl phosphate and DCC.

Ether and thioether-phosphatidic acids are prepared by total chemical synthesis utilizing 1,2-isopropylideneglycerol and 1-thioglycerol, respectively.

DETAILED DESCRIPTION OF THE PREFERRED EMBODIMENTS OF THE INVENTION

The following specific embodiments are set forth to illustrate the preparation and use of the compounds of the present invention. Unless otherwise indicated, all parts and percentages are by weight.

EXPERIMENTAL EXAMPLES

Synthesis of Compounds

Melting points were taken on a Mel-Temp capillary melting point apparatus. Nuclear magnetic resonance ($^1$H NMR) spectra were recorded on a Varian Associates EM-390 spectrometer. The chemical shift values were expressed in values (parts per million) relative to tetramethylsilane as an internal standard. AG1-X8 (Bio-Rad), diethylaminoethyl-cellulose (DE-52, Whatman), Dowex 50W-X8 (Bio-Rad), and Amberlite CG-50 (Sigma) were used for column chromatography. Evaporation was performed in vacuo at 30° C. TLC was performed on glass plates coated with a 0.25 mm layer of silica gel PF-254 (Brinkman) and on polygram sil G/UV 254 (Brinkman) using the following solvent systems: (A) $CHCl_3$-MeOH (95:5), (B) $CHCl_3$—MeOH—$H_2O$—HOAc (25:15:4:2), (C) i—PrOH—$H_2O$ concentrated $NH_4OH$ (7:2:1), and (D) $CHCl_3$—MeOH—$H_2O$ (10:10:1). UV-absorbing compounds were detected by visualization under a UV lamp (254 nm) and phosphorus-containing compounds will be detected with a modified Dittmar-Lester spray (Ryu, E. K. and MacCoss, M. J. *Lipid Res.* 20, 651, 1979). The organic compounds were also detected by charring after spraying with the above reagent.

EXAMPLE 1

Figure 1:
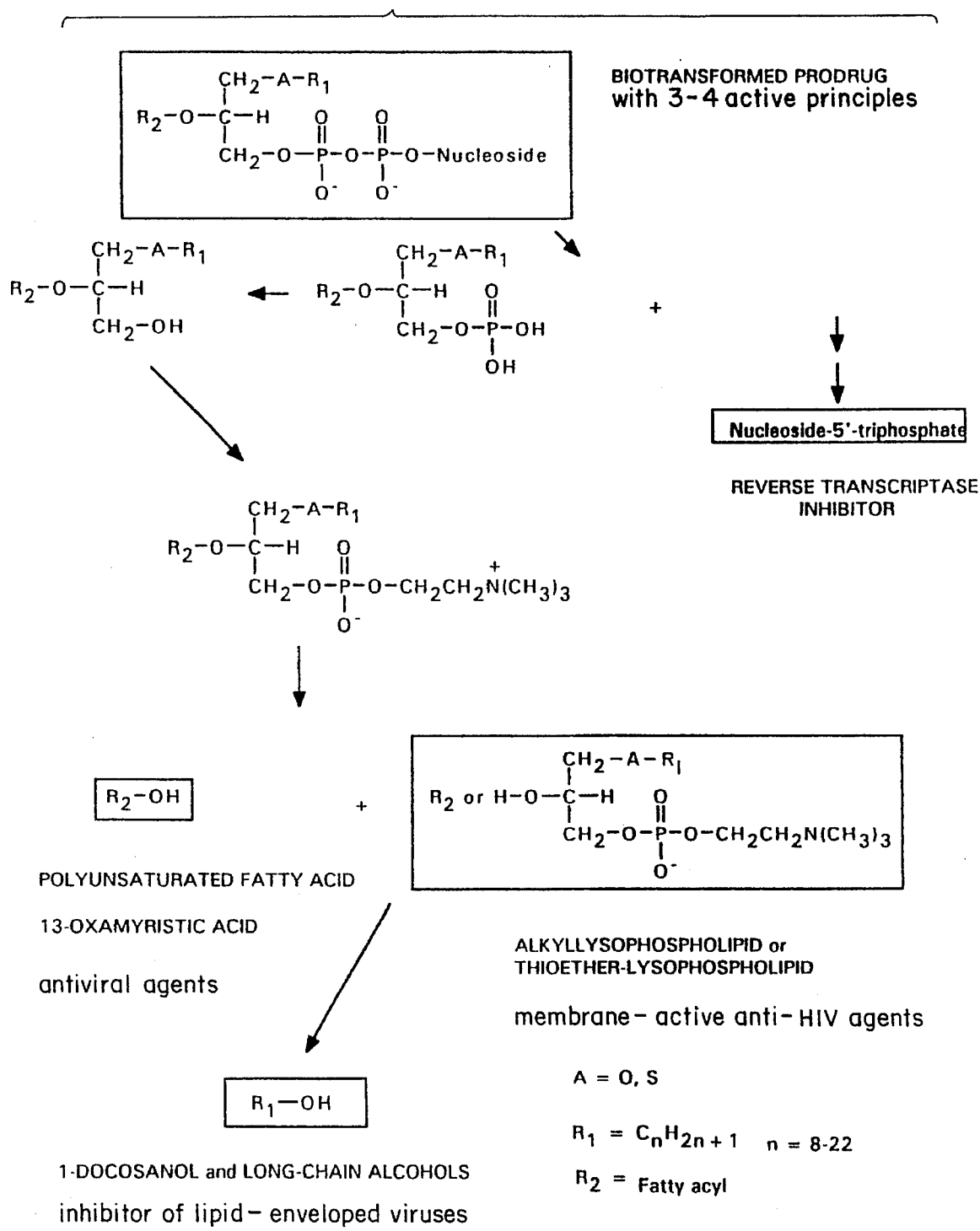
FIG. 1. Proposed degradative metabolism of the conjugate showing biotransformed prodrug conjugate with 3–4 active principles having sustained release, resistance to catabolic degradation and target specific delivery.
Figure 2:
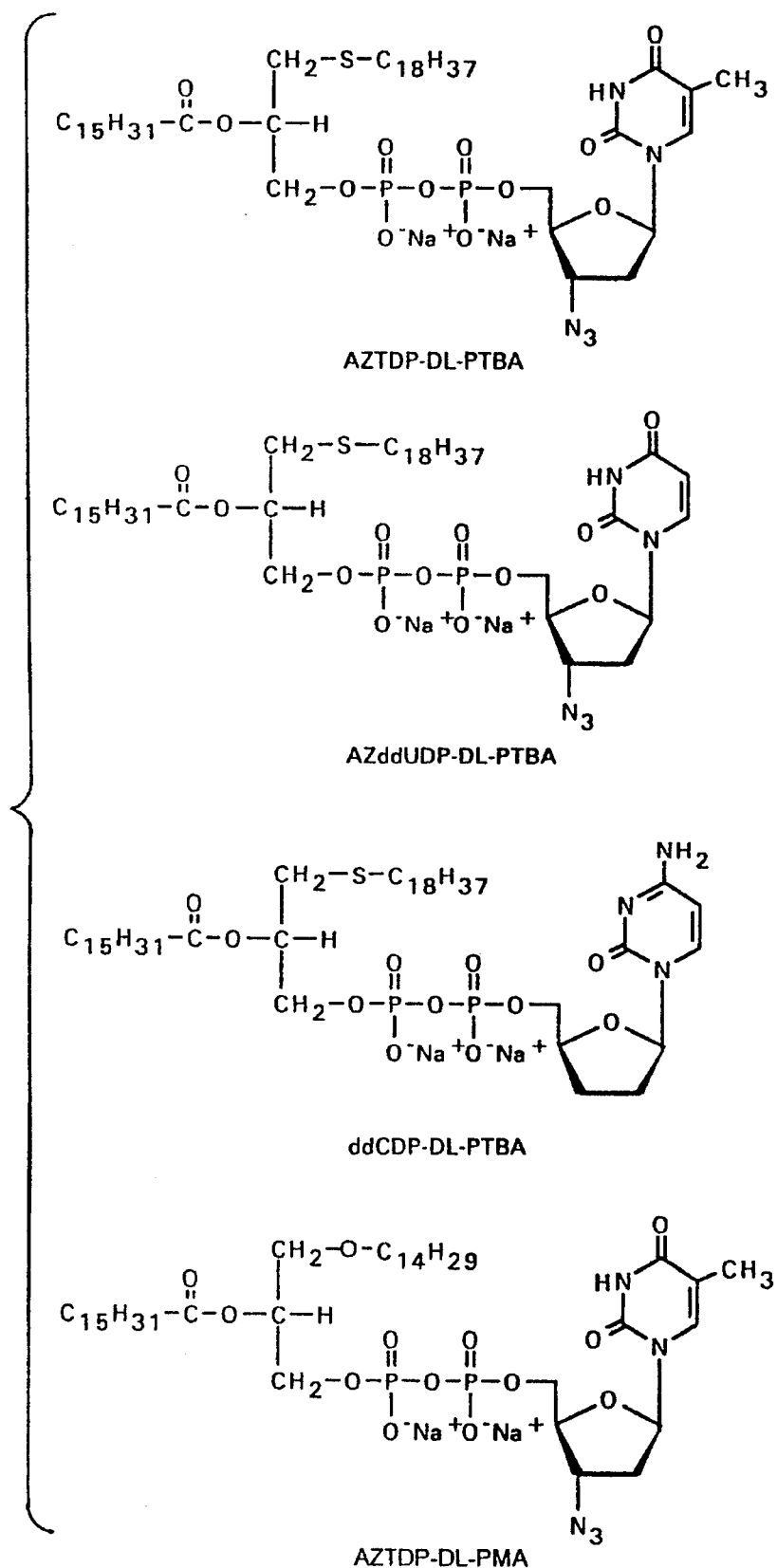
FIG. 2. Structures of anti-HIV nucleoside conjugates.

3'-Azido-3'-deoxythymidine-5'-diphosphate-rac-1-S-octadecyl-O-palmitoyl- 1-thioglycerol (AZTDP-DL-PTBA) (FIG. 2)

An anhydrous mixture of 1.42 g (2.0 mmol) of AZTMP morpholidate prepared by the process detailed in Hong et al. *Biochem. Biophys. Res. Commun.* 94, 1169 (1980) and 1.70 g (2.5 mmol) of rac-1-S-octadecyl-2-O-palmitoyl-1-thioglycerol 3-phosphate (Hong et al. *J. Med. Chem.* 33, 1380, 1990) in 100 ml of anhydrous pyridine was stirred at room temperature for 7 days and then evaporated to dryness. The residue was co-evaporated with toluene to remove the residual pyridine and dissolved in 200 ml of $CHCl_3$-95% ethanol-$H_2O$ (2:4:1) and 40 ml of $H_2O$ was added. The aqueous layer contained the unreacted morpholidate, which was recovered. The organic layer was separated and the aqueous layer was extracted with $CHCl_3$ (2×100 ml). The combined organic phase was extracted with 0.5N HCl (30 ml) and the aqueous layer was extracted with $CHCl_3$ (2×50 ml). The organic phase was evaporated to dryness and the residue was dissolved in 200 ml of $CHCl_3$-95% ethanol-$H_2O$ (2:4:1). The solution was then applied to a DE-52 (acetate) column (4.5×20 cm). The column was eluted first with 1000 ml of the same solvent and then 7000 ml of 0.02M ammonium acetate in the same solvent. Fractions of 950–1550 ml of 0.02M ammonium acetate were pooled and kept at 0°–3° C. overnight. White solid (the phosphatidic acid) was removed by filtration and the filtrate was quickly evaporated to a small volume. The white solid was filtered and washed with 50% aqueous acetone and then with acetone. The solid ($NH_4$ salt of the conjugate) was dissolved in $CHCl_{3-95}$% ethanol-H$_2$O (2:4:1) and the solution was passed through an Amberlite CG-50 (Na$^+$) column (2.5× 10 cm). The column was eluted with the same solvent until no UV-absorbing compound was detected. The combined eluate was cooled at 0°–3° C. overnight and the white solid (more phosphatidic acid) was removed by filtration. The filtrate was evaporated to a small volume and the product was filtered, washed with acetone, and dried in vacuo over P$_2$O$_5$. the conjugate as Na salt weighed 566 mg (27% yield); mp 199°–201° C. dec.; $^1$H NMR (CDCl$_3$—CD$_3$OD, 1:1) δ0.94 (6, dt, J=7 Hz, terminal 2 CH$_3$), 1.34–1.43 (54, m, (CH$_2$)$_{15}$, (CH$_2$)$_{12}$), 1.57–1.73 (4, m, SCH$_2$CH$_2$, COCH$_2$CH$_2$), 2.01 (3, s, thymine CH$_3$), 2.41 (2, m, H-2'), 2.64 (2, m, CH$_2$CH$_2$CO), 2.77 (2, m, SCH$_2$CH$_2$), 2.91 (2, dd, J=5 Hz), 4.07–4.14 (3, m, H-4', 3—CH$_2$), 4.24 (2, m, H-5'), 4.65 (1, t, J=3.3 Hz, H-3'), 5.21 (1, quintet, J=6 Hz, 2-CH), 6.21 (1, t. J=6 Hz, H-1'), 7.71 (1, s, thymine H-6).

Anal. Calculated for C$_{47}$H$_{85}$N$_5$O$_{12}$SP$_2$.2Na.3H$_2$O: C, 51.87; H, 8.24; N, 6.43; S, 2.95; P, 5.69. Found C, 51.91; H, 8.35; N, 5.29; S, 3.30; P, 5.34.

EXAMPLE 2

3'-Azido-2',3'-dideoxyuridine-5'-diphosphate-rac-1-S-octadecyl-2-O-palmitoyl- 1-thioglycerol
(AZddUDP-DL-PTBA) (FIG. 2)

Using the process of Example 1, this compound was prepared by substituting AZddUMP morpholidate for AZTMP morpholidate in 13.4% yield; mp 185°–187° C.

Anal. Calculated for C$_{46}$H$_{83}$N$_5$O$_{12}$O$_{12}$SP$_2$.2Na.H$_2$O: C, 52.31; H, 8.11; N, 6.63; S, 3.04; P, 5.87. Found C, 52.51; H, 8.22; N, 5.42; S, 3.49; P, 5.71.

EXAMPLE 3

2',3'-Dideoxycytidine-5'-diphosphate-rac-1-S-octadecyl-2-O-palmitoyl- 1-thioglycerol
(ddCDP-DL-PTBA) (FIG. 2)

Using the process of Example 1, this compound was prepared by substituting ddCMP morpholidate for AZTMP morpholidate in 13.7% yield; mp 198°–200° C.

Anal. Calculated for C$_{46}$H$_{85}$N$_3$O$_{11}$SP$_2$.2Na.H$_2$O: C, 53.52; H, 8.69; N, 4.07; S, 3.11; P, 6.00. Found C, 53.57; H, 9.17; N, 3.79; S, 3.05; P, 5.77.

EXAMPLE 4

3'-Azido-3'-deoxythymidine-5'-diphosphate-rac-1-O-tetradecyl-2-O-palmitoylglycerol
(AZTDP-DL-PMA) (FIG. 2)

1) rac-1-O-Tetradecylglycerol

To a mixture of Solketal (66.1 g, 0.5 mol), 1-bromotetradecane (159.4 g, 0.575 mol), and DMF (800 ml) was added 60% NaH (26.0 g, 0.65 mol) in oil dispersion in 3 portions for 1 hr. The mixture was stirred at room temperature for 1 day and methanol (20 ml) was added to destroy the excess NaH. This was then poured into 1500 ml of ice-water and the aqueous layer was extracted with hexanes (2000 ml). The combined organic layers were evaporated to dryness and the oily residue was refluxed in 10% HCl/methanol (conc. HCl, 250 ml and methanol, 675 ml) for 30 min followed by stirring at room temperature overnight. The white flaky solid was filtered and washed with methanol (122 g). The additional product was obtained from the filtrate (5.7 g); Total 127.7 g (88.5%). The crude product was recrystallized from diethyl ether; Yield 99.7 g (69.1%), mp 57°–58° C.

Anal. Calculated for C$_{17}$H$_{36}$O$_3$: C, 70.78; H, 12.58. Found C, 70.81; H, 12.29.

2) rac-1-O-Tetradecyl-3-O-(tert-butyldimethylsilyl)glycerol

A mixture of rac-1-O-tetradecylglycerol (57.7 g, 0.2 mol), tert-butyldimethylsilyl chloride (33.2 g, 0.22 mol), imidazole (30.0 g, 0.44 mol), and DMF (300 ml) was stirred at room temperature for 1 day. The solvent was evaporated to dryness in vacuo at 70° C. and the residue was partioned between H$_2$O and diethyl ether (500 ml each). The organic layer was dried over Na$_2$SO$_4$ and then evaporated to dryness. The oily residue was further evaporated by using a high vacuum at 70° C. The crude product, essentially homogeneous by TLC, was used for the next step without further purification (100% yield).

3) rac-1-O-Tetradecyl-2-O-palmitoylglycerol

To a mixture of rac-1-O-tetradecyl-3-O-(tert-butyldimethylsilyl)glycerol (40.3 g, 0.1 mol), anhydrous pyridine (9.5 g, 0.12 mol), and toluene (300 ml) was added dropwise palmitoyl chloride (30.2 g, 0.11 mole) at room temperature at room temperature followed by stirring for 1 day. The suspension was then partitioned between diethyl ether and H$_2$O (200 ml each). The organic layer was washed with 0.5N H$_2$SO$_4$, saturated NaHCO$_3$, and H$_2$O (100 ml each) and then evaporated to dryness. The residue was boiled with 95% ethanol (1000 ml) and the suspension was kept at room temperature overnight. The supernatant was removed by decantation and the oily product was washed with cold 95% ethanol. The dried product, rac-1-O-tetradecyl-2-O-Palmitoyl- 3-O-(tert-butyldimethylsilyl)glycerol, weighed 60.3 g (94% yield).

To a mixture of this product in glacial acetic acid (13.2 ml) was added dropwise 1M tetrabutylammonium fluoride in THF (132 ml) for a period of 1 hr at 0°–5° C. and the mixture was stirred at room temperature for 1 day. The mixture was cooled at 0°–3° C. for 3 hr and wight crystals were filtered and washed with cold hexanes (33 g, 66.6% yield). This was recrystallized from 95% ethanol (1000 ml); 24.5g, 49.5% yield, mp 61°–62° C.

Anal. Calculated for C$_{33}$H$_{66}$O$_4$: C, 75.23; H, 12.63. Found C, 74.97; H, 12.54.

4) rac-1–0-Tetradecyl-2-O-palmitoylglycerol 3-phosphate

To an ice-cold mixture of POCl$_3$ (9.2 g, 0.06 mol) and hexanes (25 ml) was added dropwise triethylamine (6.07 g, 0.06 mol) in hexanes (25 ml). To the mixture was added dropwise a solution of dried rac-1-O-tetradecyl-2-O-palmitoylglycerol (21.1 g, 0.04 mol) in toluene (500 ml) at 0°–5° C. over a period of 1 hr, and then the mixture was stirred at room temperature overnight. Water (100 ml) was added to the mixture and the suspension was stirred at room temperature for 1 hr. The mixture was then partitioned between diethyl ether (500 ml) and H$_2$O (200 ml). The organic layer was dried over Na$_2$SO$_4$ and evaporated to dryness. The residue was crystallized from hexanes at 0°–5° C. (15.2 g, 62.7% yield). The analytical sample was recrystallized from diethyl ether at room temperature; mp 60°–64° C. wet and 74°–84° C. slowly melt.

5) Condensation

Using the process of Example 1, this compound was prepared by substituting rac-1-S-octadecyl-2-O-palmitoyl-1-thioglycerol 3-phosphate for rac-1-O-tetradecyl-2-O-palmitoylglycerol 3-phosphate in 19.1% yield; mp 174°–176° C. soften and 197°–199° C. dec.

Anal. Calculated for $C_{43}H_{77}O_{13}N_5P_2 \cdot 2Na \cdot 2H_2O$: C, 50.83; H, 8.04; P, 6.10. Found C, 51.00; H, 8.12; P, 6.15.

EXAMPLE 5

Formulation

Solubility of AZTDP-DL-PTBA in water is only 0.58 mM. Thus, the compounds in the present invention were formulated in a micellar solution by sonication for the biological testings such as anti-HIV screenings. The compound was suspended in sterile water and then sonicated using a Branson Sonifier Cell Disruptor 200 at control 2-3 for 5 min (temp 20°–60° C.). The solution was sterile-filtered through a 0.22 μm membrane filter into a sterile receiving container under a laminar flow cabinet. The compound was existed as micelles and the micellar solution was stored in a refrigerator.

Biological Data

EXAMPLE 6

Anti-HIV Assay (FIGS. 3–6)

Anti-HIV evaluation for the compounds was performed at the National Cancer Institute, National Institute of Health and is presented in FIGS. 3–6. The results indicate that AZTDP-DL-PTBA of the present invention has produced a strong in vitro anti-HIV activity.

The procedure is designed to detect agents acting at any stage of the virus reproductive cycle (Weislow, et al., *J. Natl. Cancer Inst.* 81, 577, 1989). The assay basically involves the killing of T4 lymphocytes by HIV. Small amounts of HIV are added to cells, and a complete cycle of virus reproduction is necessary to obtain the required cell killing. Agents that interact with virions, cells, or virus gene-products to interfere with viral activities will protect cells from cytolysis. Compounds that degenerate or are rapidly metabolized in the culture conditions may not show activity in this screen. All tests are compared with at least one positive (e.g., AZT-treated) control done at the same time under identical conditions.

Compound was dissolved in DMSO then diluted 1:100 in cell culture medium before preparing serial half-$log_{10}$ dilutions. T4 lymphocytes (CEM cell line) were added and after a brief interval HIV-1 was added, resulting in a 1:200 final dilution of the compound. Uninfected cells with the compound served as a toxicity control, and infected and uninfected without the compound served as basic controls. Cultures were incubated at 37° C. in a 5% $CO_2$ atmosphere for 6 days. The tetrazolium salt, XTT, was added to the wells, and cultures were incubated to allow formazan color development by viable cells. Individual wells were analyzed spectrophotometrically to quantitate formazan production, and in addition were viewed microscopically for detection of viable cells and confirmation of protective activity. Drug-treated virus-infected cells were compared with drug-treated noninfected cells and with other appropriate controls (untreated infected and untreated noninfected cells, drug-containing wells without cells, etc.) on the same plate. Data were reviewed in comparison with other tests done at the same time and a determination about activity was made.

Figure 3:
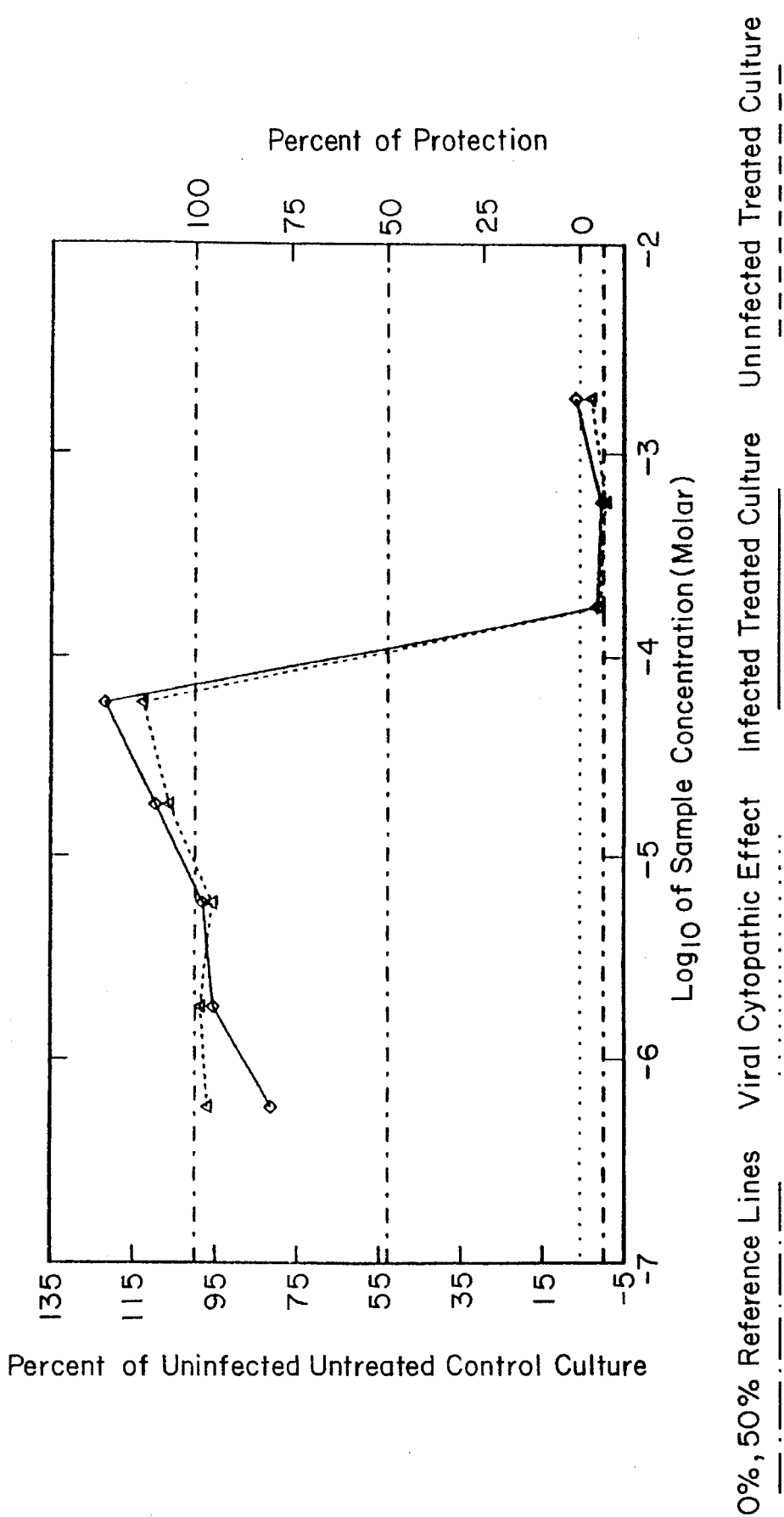
FIG. 3. Anti-HIV activity of AZTDP-DL-PTBA from the National Cancer Institute Developmental Therapeutics Program In-Vitro Testing Results; NSC 648540-S/1; Plate 5440; Lab 9N; SSPL:129N; Primary Screen Assay; Test Date, Jan. 21, 1992; Solubility Ind.: 1; Report Date, Apr. 27, 1992; Cell Line, CEM-IW; Solvent: Saline<0.9% (MEDIA). Numerical results are shown in Table 1.
Figure 4:
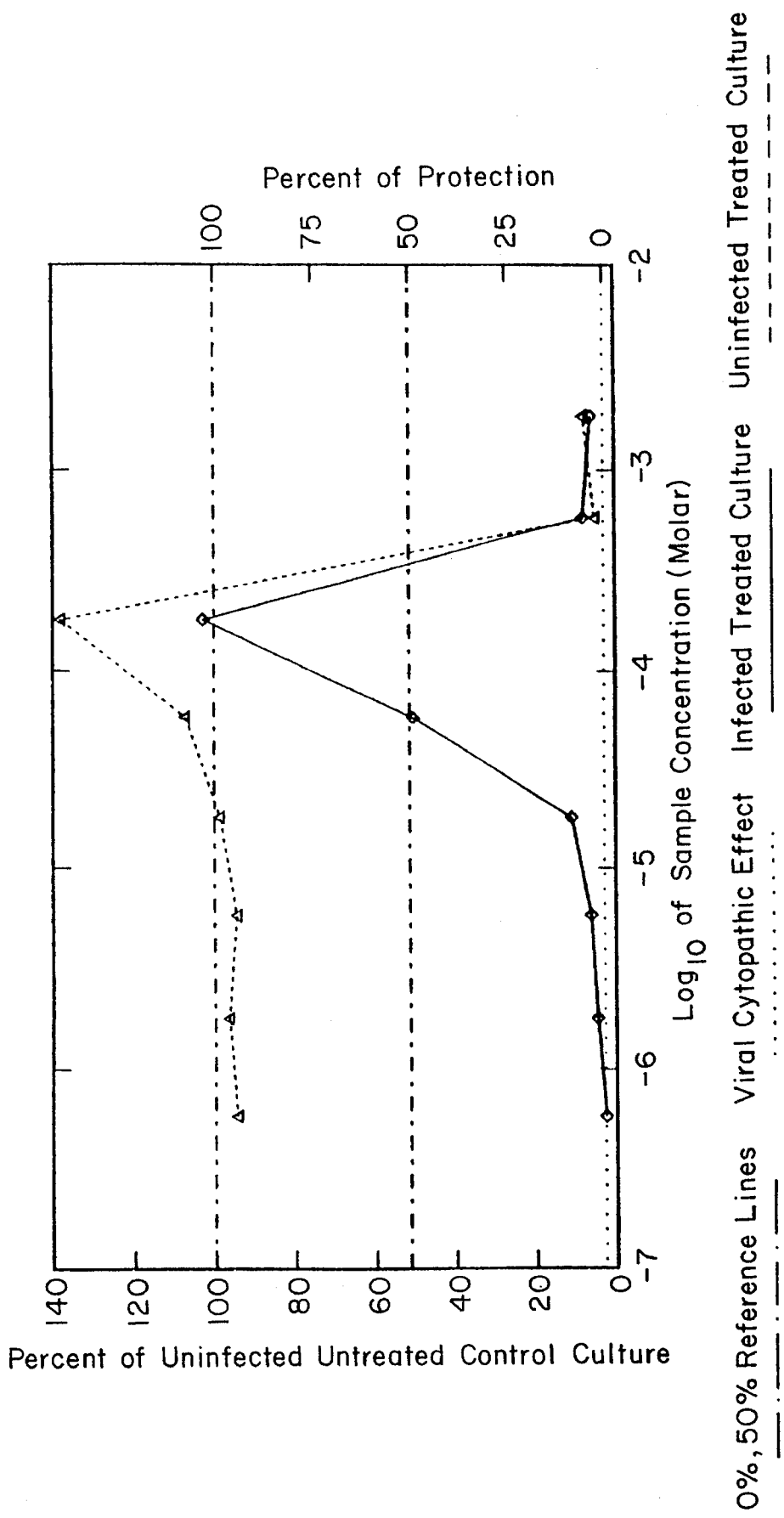
FIG. 4. Anti-HIV activity of AZddUDP-DL-PTBA from the National Cancer Institute Developmental Therapeutics Program In-Vitro Testing Results; NSC: 648541-T/1; Plate 5466; Lab 9N; SSPL: 129N; Primary Screen Assay; Test Date, Jan. 21, 1992; Solubility Ind.: 1; Report Date, Apr. 27, 1992; Cell Line: CEM-IW; Solvent: Saline<0.9% (MEDIA). Numerical results are shown in Table 2.
Figure 5:
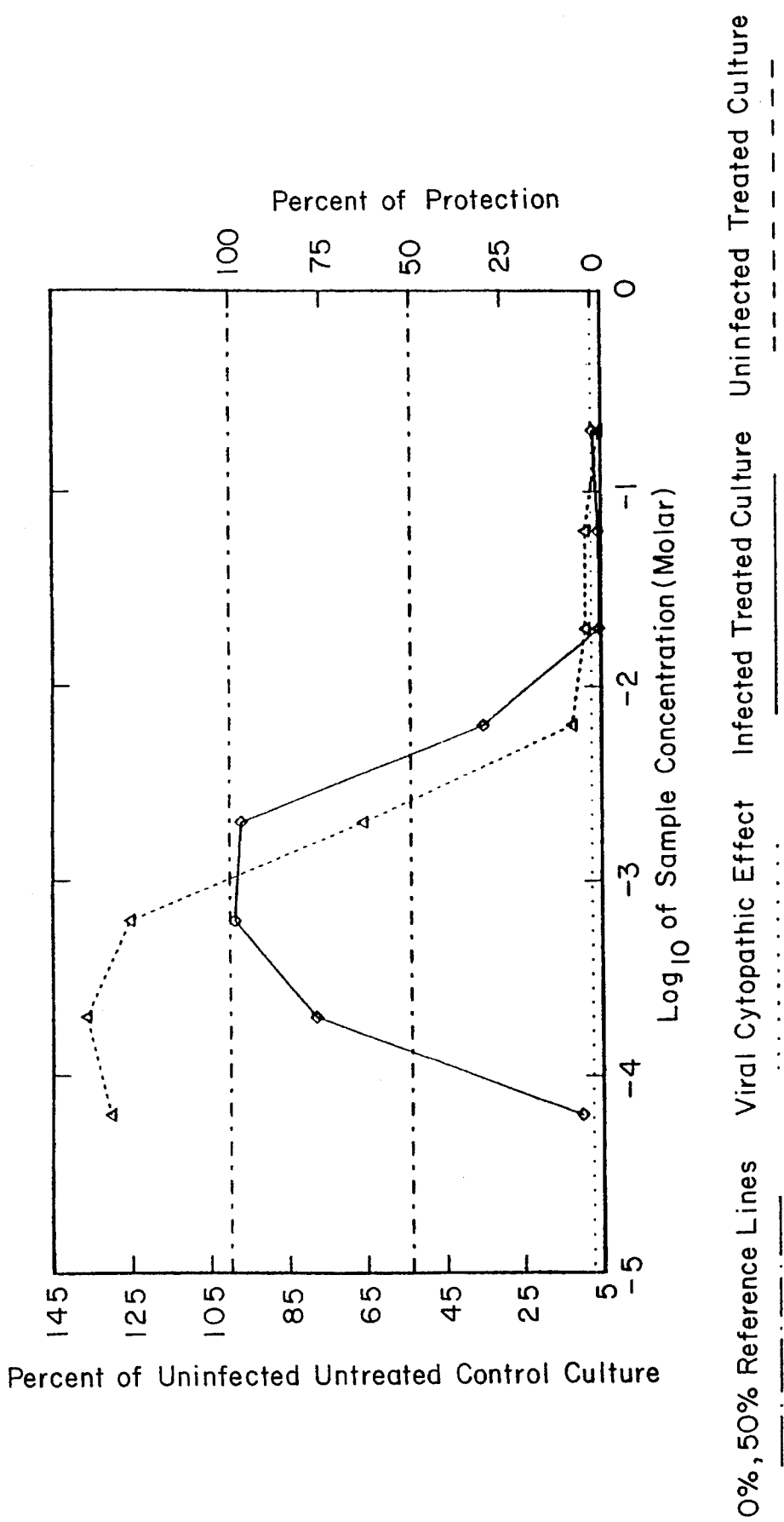
FIG. 5. Anti-HIV activity of ddCDP-DL-PTBA from the National Cancer Institute Developmental Therapeutic Program In-Vitro Testing Results; NSC: D- 652872-A/1; Plate 24; Lab 9N; Primary Screen Assay; Test Date, Jul. 23, 1992; Solubility Ind.: 1; Report Date: Aug. 7, 1992; Cell Line: CEM-IW; Solvent: Saline<0.9% (MEDIA). Numerical results are shown in Table 3.
Figure 6:
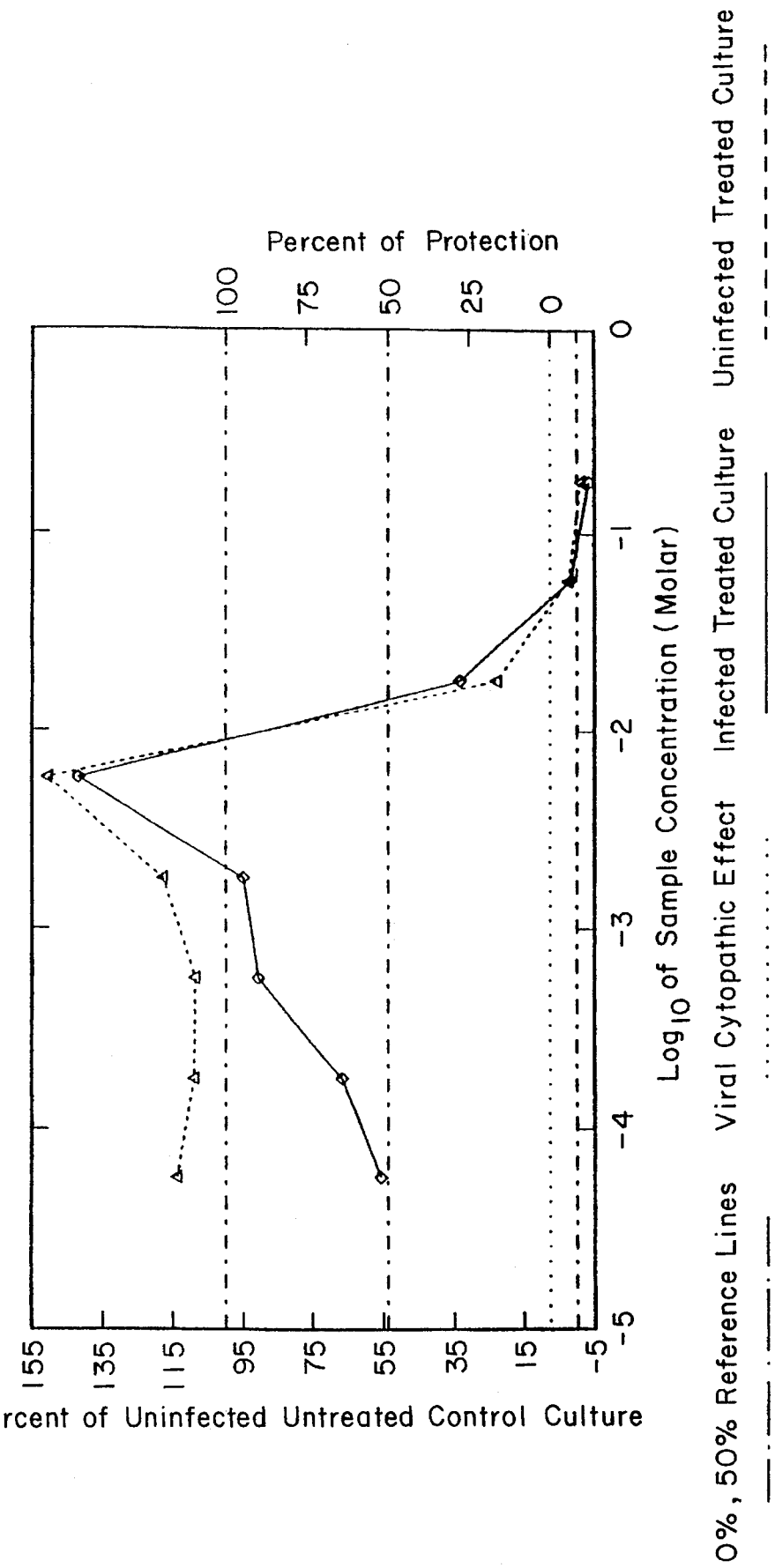
FIG. 6. Anti-HIV activity of AZTDP-DL-PMA from the National Cancer Institute Developmental Therapeutics Program In-Vitro Testing Results; NSC: D- 652873-C/1; Plate 24; Lab 9N; SSPL: 129N; Primary Screen Assay; Test Date, Jul. 23, 1992; Solubility Ind.: 1; Report Date, Sep. 11, 1992; Cell Line: CEM-IW; Solvent: Saline<0.9% (MEDIA). Numerical results are shown in Table 4.

FIG. 3 shows the in vitro anti-HIV drug screening results for AZTDP-DL-PTBA. AZTDP-DL-PTBA protected 80% of HIV-infected CEM cells at as low as $5.80 \times 10^{-7}$M and lost the protection at $1.80 \times 10^{-4}$M, while the compound started to show the cytotoxicity at $10^{-4}$M ($IC_{50}=1.10 \times 10^{-4}$). The results have concluded that AZTDP-DL-PTBA is "active" as anti-HIV drug. AZddUDP-DL-PTBA, ddCDP-DL-PTBA, and AZTDP-DL-PMA gave 50% of the protection ($EC_{50}$) at $5.90 \times 10^{-5}$M, $1.30 \times 10^{-4}$M, and $5.70 \times 10^{-5}$ M, respectively, and reported as "moderate". These drugs started to show the cytotoxicity ($IC_{50}$) at $3.90 \times 10^{-4}$M, $2.80 \times 10^{-3}$M, and $1.40 \times 10^{-2}$M, respectively.

AZTDP-DL-PTBA was also tested for in vivo cytotoxicity against i.p. implanted L1210 lymphoid leukemia ($10^6$ cells) in DBA/2J mice. Administrations (i.p.) of 100–300 mg (95–285 μmole)/kg of AZTDP-DL-PTBA to the leukemic mice did not increase their life span (% ILS=0). Toxicity as reflected in weight loss was observed.

Since the previous antitumor nucleoside conjugates of ether and thioether phospholipids have been much more effective in in vivo than in vitro antitumor testings, the compounds of the present invention will also be very effective as in vivo anti-HIV drugs with improved therapeutic index.

EXAMPLE 7

Figure 7:
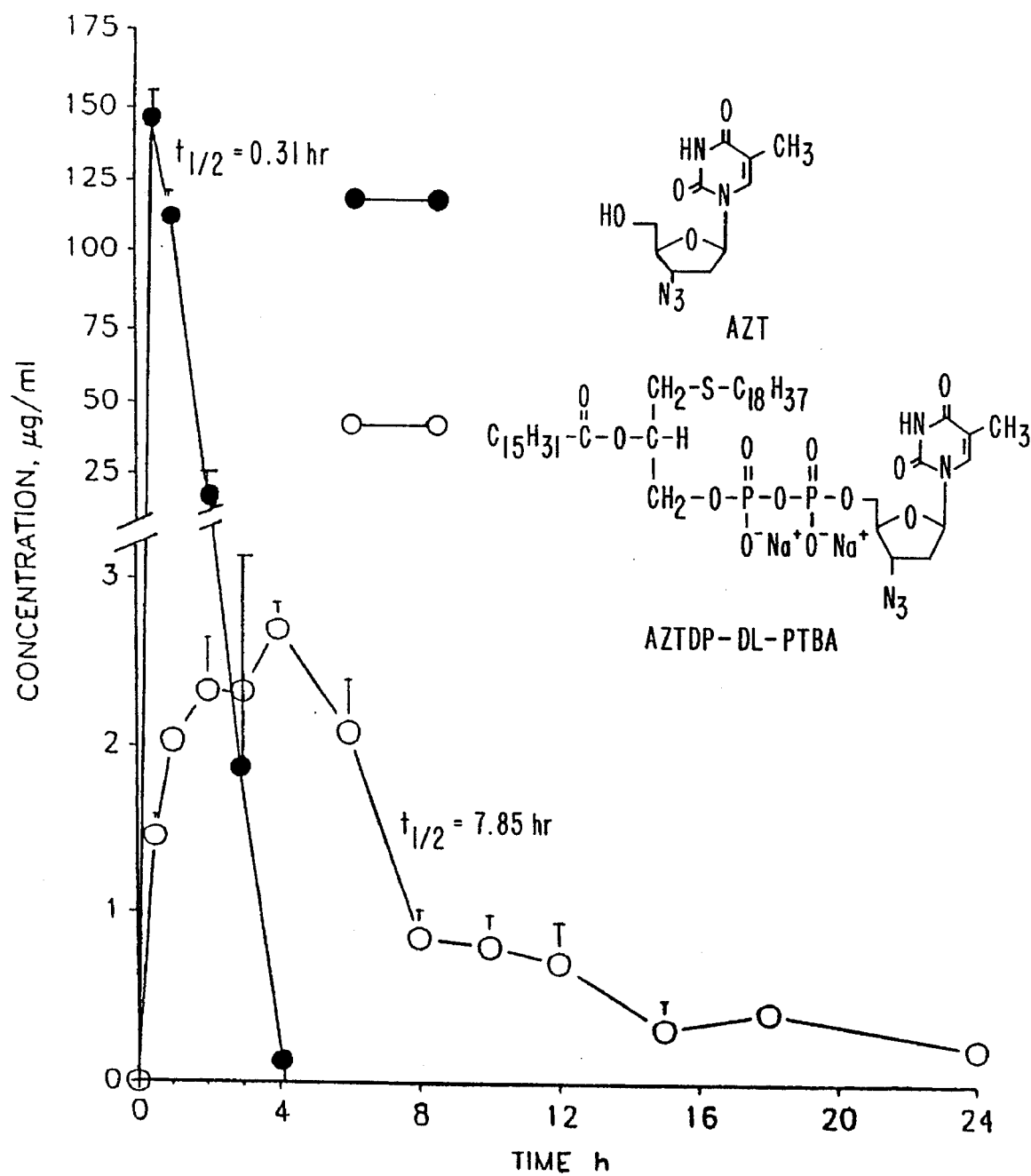
FIG. 7. Mouse serum concentration of AZT following administration of AZT or AZTDP-DL-PTBA Female NIH-Swiss mice weighing 25–30 g were administered i.p. with AZT (100 mg/kg) or AZTDP-DL-PTBA (394 mg/kg, equivalent to 100 mg/kg AZT). Three mice were sacrificed at the designated time (up to 24 hr) and AZT in the serum was analyzed by a HPLC method.

Pharmacokinetics (FIG. 7)

Female NIH-Swiss mice weighing 25–30 g were administered intraperitoneally (i.p.) with 394 mg/kg of AZTDP-DL-PTBA (equivalent to 100 mg/kg AZT). Three mice were sacrificed at the designated time (up to 24 hours) and AZT in the serum was analyzed by an HPLC method. Comparison of the apparent serum half-lives for AZT (7.85 vs 0.31 hr) after AZTDP-DL-PTBA and AZT administration indicates an increased retention of AZT in the serum following conjugate administration compared to the value obtained for parent drug administration (FIG. 7). AZT level in the serum after AZTDP-DL-PTBA administration rose a maximum 2.70 μg/ml at 4 hr and slowly decreased over a period of 24 hr (0.22 μg/ml at 24 hr), while that after AZT administration completely disappeared in 4 hr. The intact conjugate level in the serum was unable to be checked by the HPLC method. The initial lower AZT level after the conjugate administration compared to that after AZT might be due to the majority of the conjugate being bound to the various cells and serum albumin.

While the invention has been described in conjunction with specific examples thereof, this is illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

TABLE 1

| SUMMARY | | | INFECTED RESPONSE | UNINFECTED RESPONSE |
|---|---|---|---|---|
| Index | Concentration | DOSE (Molar) | Percent of Control | Percent of Control |
| IC50(Molar) | $1.10 \times 10^{-4}$ | $5.80 \times 10^{-7}$ | 81.58 | 97.00 |
| EC50(Molar) | | $1.80 \times 10^{-6}$ | 95.62 | 98.74 |
| TI50(IC/EC) | | $5.80 \times 10^{-6}$ | 98.14 | 95.86 |
| Conclusion | | $1.80 \times 10^{-5}$ | 109.67 | 106.37 |
| CONFIRMED ACTIVE | | $5.80 \times 10^{-5}$ | 121.85 | 112.61 |
| | | $1.80 \times 10^{-4}$ | 1.53 | 0.90 |
| | | $5.80 \times 10^{-4}$ | 0.57 | −0.54 |
| | | $1.80 \times 10^{-3}$ | 6.81 | 3.00 |

TABLE 2

| SUMMARY | | | INFECTED RESPONSE | UNINFECTED RESPONSE |
|---|---|---|---|---|
| Index | Concentration | DOSE (Molar) | Percent of Control | Percent of Control |
| IC50(Molar) | $5.90 \times 10^{-4}$ | $5.80 \times 10^{-7}$ | 2.69 | 94.56 |
| EC50(Molar) | $5.90 \times 10^{-5}$ | $1.80 \times 10^{-6}$ | 4.68 | 96.57 |
| TI50(IC/EC) | $6.60 \times 10^{8}$ | $5.80 \times 10^{-6}$ | 6.20 | 94.56 |
| Conclusion | | $1.80 \times 10^{-5}$ | 11.06 | 98.64 |
| CONFIRMED ACTIVE | | $5.80 \times 10^{-5}$ | 50.56 | 107.17 |
| | | $1.80 \times 10^{-4}$ | 102.77 | 138.12 |
| | | $5.80 \times 10^{-4}$ | 7.96 | 5.01 |
| | | $1.80 \times 10^{-3}$ | 5.99 | 7.85 |

TABLE 3

| SUMMARY | | | INFECTED RESPONSE | UNINFECTED RESPONSE |
|---|---|---|---|---|
| Index | Concentration | DOSE (Molar) | Percent of Control | Percent of Control |
| IC50(Molar) | $2.80 \times 10^{-3}$ | $6.30 \times 10^{-5}$ | 10.22 | 130.37 |
| EC50(Molar) | $1.30 \times 10^{-4}$ | $2.00 \times 10^{-4}$ | 77.98 | 136.55 |
| TI50(IC/EC) | $2.10 \times 10^{+1}$ | $6.30 \times 10^{-4}$ | 98.73 | 125.40 |
| Conclusion | | $2.00 \times 10^{-3}$ | 97.05 | 65.79 |
| CONFIRMED ACTIVE | | $6.30 \times 10^{-3}$ | 35.24 | 12.46 |
| | | $2.00 \times 10^{-2}$ | 5.53 | 9.00 |
| | | $6.30 \times 10^{-2}$ | 5.72 | 9.09 |
| | | $2.00 \times 10^{-1}$ | 7.12 | 5.62 |

TABLE 4

| SUMMARY | | | INFECTED RESPONSE | UNINFECTED RESPONSE |
|---|---|---|---|---|
| Index | Concentration | DOSE (Molar) | Percent of Control | Percent of Control |
| IC50(Molar) | $1.40 \times 10^{-2}$ | $5.70 \times 10^{-5}$ | 55.76 | 113.78 |
| EC50(Molar) | | $1.80 \times 10^{-4}$ | 66.82 | 109.00 |
| TI50(IC/EC) | | $5.70 \times 10^{-4}$ | 90.67 | 108.72 |
| Conclusion | | $1.80 \times 10^{-3}$ | 94.99 | 117.71 |
| CONFIRMED ACTIVE | | $5.70 \times 10^{-3}$ | 141.80 | 150.52 |
| | | $1.80 \times 10^{-2}$ | 33.22 | 22.68 |
| | | $5.70 \times 10^{-2}$ | 1.73 | 2.25 |
| | | $1.80 \times 10^{-1}$ | −3.42 | −1.12 |

What is claimed is:

1. A compound having the formula:

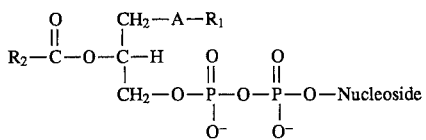

wherein:

- $R_1$ is selected from the group consisting of alkyls and alkenyls containing from 8 to 22 carbon atoms;
- A is selected from the group consisting of O and S atoms;
- $R_2$ is selected from the group consisting of alkyls, hetero atom containing alkyls, and alkenyls containing from 8 to 22 carbon atoms; and the
- Nucleoside is an antiviral nucleoside selected from the group consisting of 2',3'-dideoxynucleosides, 3'-azido-2',3'-dideoxynucleosides, and 2',3'-didehydro- 2',3'-dideoxynucleosides.

2. The compound according to claim 1, wherein the $R_2$ alkyls are heteroatom-containing alkyls.

3. The compound according to claim 2, wherein the heteroatom-containing alkyls are chosen from the group consisting of $CH_3\text{—}O\text{—}(CH_2)_{10}CH_2$ and $CH_3CH_2\text{—}S\text{—}(CH_2)_{10}$.

4. The compound according to claim 1, wherein the $R_2$ alkenyls are polyunsaturated alkenyls.

5. The compound according to claim 4, wherein the polyunsaturated alkenyls are chosen from the group consisting of $CH_3(CH_2)_2(CH_2CH\text{=}CH)_2(CH_2)_7$, 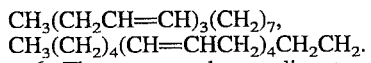

6. The compound according to claim 1, wherein the 2',3'-dideoxynucleosides are chosen from the group consisting of 2',3'-dideoxycytidine (ddC), 2',3'-dideoxyinosine (ddI), 2',3'-dideoxyadenosine (ddA), and 3'-deoxythymidine (ddT).

7. The compound according to claim 1, wherein the 3'-azido- 2',3'-dideoxynucleosides are chosen from the group consisting of 3'-azido-3'-deoxythymidine (AZT) and 3'-azido-2',3'-dideoxyuridine (AZddU).

8. The compound according to claim 1, wherein the 2',3'-didehydro- 2',3'-dideoxynucleosides are chosen from the group consisting of 2',3'-didehydro-3'-deoxythymidine (D4T) and 2',3'-didehydro- 2',3'-dideoxycytidine (D4C).

9. The compound of claim 1 formulated in a micellar solution.

10. A compound according to claim 1 which is 3'-azido-3'-deoxythymidine- 5'-diphosphate-rac-1-S-octadecyl-2-O-palmitoyl-1-thioglycerol (AZTDP-DL-PTBA).

11. A compound according to claim 1 which is 3'-azido-2',3'-dideoxyuridine- 5'-diphosphate-rac-1-S-octadecyl-2-O-palmitoyl-1-thioglycerol (AZddUDP-DL-PTBA).

12. A compound according to claim 1 which is 2',3'-dideoxycytidine- 5'-diphosphate-rac-1-S-octadecyl-2-O-palmitoyl-1-thioglycerol (ddCDP-DL-PTBA).

13. A compound according to claim 1 which is 3'-azido-3'-deoxythymidine- 5'-diphosphate-rac-1-O-tetradecyl-2-O-palmitoylglycerol (AZTDP-DL-PMA).

\* \* \* \* \*